United States Patent
Dschietzig

(10) Patent No.: US 12,226,455 B2
(45) Date of Patent: Feb. 18, 2025

(54) MEDICAL COMPOSITION FOR TREATING CARDIAC WASTING AND CACHEXIA

(71) Applicant: RELAXERA Pharmazeutische GmbH & Co. KG, Bensheim (DE)

(72) Inventor: Thomas Bernd Dschietzig, Berlin (DE)

(73) Assignee: RELAXERA PHARMAZEUTISCHE GMBH & CO. KG, Bensheim (DE)

( * ) Notice: Subject to any disclaimer, the term of this patent is extended or adjusted under 35 U.S.C. 154(b) by 0 days.

(21) Appl. No.: 17/776,749

(22) PCT Filed: Nov. 16, 2020

(86) PCT No.: PCT/EP2020/082308
§ 371 (c)(1),
(2) Date: May 13, 2022

(87) PCT Pub. No.: WO2021/094626
PCT Pub. Date: May 20, 2021

(65) Prior Publication Data
US 2022/0401522 A1   Dec. 22, 2022

(30) Foreign Application Priority Data
Nov. 16, 2019   (DE) .................. 10 2019 131 002.4

(51) Int. Cl.
*A61K 38/22* (2006.01)
*A61P 9/02* (2006.01)
*A61P 9/04* (2006.01)

(52) U.S. Cl.
CPC .......... *A61K 38/2221* (2013.01); *A61P 9/02* (2018.01)

(58) Field of Classification Search
CPC ....... A61K 38/2221; A61K 38/22; A61P 9/02; A61P 9/04
See application file for complete search history.

(56) References Cited

U.S. PATENT DOCUMENTS

| 9,616,171 B2 | 4/2017 | Qin et al. |
| 2015/0233945 A1* | 8/2015 | Block .................. A61P 9/04 435/7.92 |

FOREIGN PATENT DOCUMENTS

| AU | 2016219717 A1 | 9/2016 |
| CN | 104922661 B | 8/2018 |
| WO | WO 2009/140657 A2 | 11/2009 |

OTHER PUBLICATIONS

Bani D., "Recombinant human H2 relaxin (serelaxin) as a cardiovascular drug: aiming at the right target," Drug Discovery Today, Jul. 2020, 25(7): 1239-1244. (Year: 2020).*
Anker et al., "The syndrome of cardiac cachexia," International Journal of Cardiology, vol. 85, 2002, pp. 51-66.
Azhar et al., "New Approaches to Treating Cardiac Cachexia in the Older Patient," Curr Cardiovasc Risk Rep, vol. 7, 2013 (Published online Oct. 26, 2013), pp. 480-484.
Dschietzig et al., "Relaxin improves TNF-α-induced endothelial dysfunction: the role of glucocorticoid receptor and phosphatidylinositol 3-kinase signalling," Cardiovascular Research, vol. 95, 2012, pp. 97-107.
Dschietzig et al., "The Positive Inotropic Effect of Relaxin-2 in Human Atrial Myocardium is Preserved in End-Stage Heart Failure: Role of Gi-Phosphoinositide-3 Kinase Signaling," Journal of Cardiac Failure, vol. 17, No. 2, 2011, pp. 158-166.
Florea et al., "The cardiac component of cardiac cachexia," American Heart Journal, Jul. 2002, pp. 45-50.
International Preliminary Report on Patentability dated May 17, 2022, and Written Opinion of the International Searching Authority for International Application No. PCT/EP2020/082308, dated Feb. 18, 2021.
International Search Report for International Application No. PCT/EP2020/082308, dated Feb. 18, 2021.
Michel et al., "Biomarkers for the detection of apparent and subclinical cancer therapy-related cardiotoxicity," Journal of Thoracic Disease, vol. 10, Suppl. 35, 2018, pp. S4282-84295.
Strassburg et al., "Metabolic and immunological derangements in cardiac cachexia: where to from here?" Heart Fail Rev, vol. 11, 2006, pp. 57-64.

* cited by examiner

*Primary Examiner* — Julie Ha
(74) *Attorney, Agent, or Firm* — Birch, Stewart, Kolasch & Birch, LLP

(57) ABSTRACT

Human relaxin-2 as active ingredient in a pharmaceutical composition for treating a subject suffering from cachexia syndrome or cardiac wasting or suspected of being at risk of suffering from cardiac wasting or cardiac decompensation is described. Also described are methods of diagnosis of cachexia and cardiac wasting and patients suspected of being at risk of suffering from cardiac decompensation. Further described is a patch pump for sc. or iv infusion of relaxin or human relaxin-2.

6 Claims, No Drawings

MEDICAL COMPOSITION FOR TREATING CARDIAC WASTING AND CACHEXIA

TECHNICAL FIELD

The present application relates to a medical composition for treating cancer-related cachexia syndrome, and to a method of treatment of patients in the hospice setting suffering from any kind of cachexia syndrome and in particular of cardiac wasting.

BACKGROUND

In the industrialized world cardiovascular disease and cancer are the leading causes of death in the ageing population and together they account for 50% of all deaths (Anker M et al, *Cancer and heart failure—more than meets the eye: common risk factors and co-morbidities* in European Journal of Heart Failure 2018. 20, 1382-1384). This number is misleading as cancer patients may die a cardiovascular death, and occasionally vice versa, but modern anti-cancer therapies may also lead to cardiovascular problems and heart failure which reduce the chances of life-prolonging therapies. To enable a terminally ill patient to die in dignity is a medical challenge. This is primarily a therapeutic problem despite of numerous issues of sociopsychological, ethical and religious nature, socioeconomic impacts and ultimately of infrastructure.

Life expectancy in cancer patients varies greatly between different cancer types but independently thereof and medical therapy, muscle strength and physical activity are important for improving survival in both cancer and heart failure. Patients with chronic diseases at terminal stages however are often severely limited and disabled by a syndrome which is not unique to oncology patients, the cachexia syndrome (2021 ICD-10-CM Diagnosis Code R64). This is a complex metabolic syndrome characterized by nutritional marasmus, involuntary weight loss, by atrophy of muscles and depletion of lean body mass associated with chronic disease (cancer, heart failure, pulmonary disease, chronic inflammatory syndromes, and others). It is characterized by a loss of more than 6% of non-edematous body weight in conjunction with malnutrition as a result of inadequate dietary intake, malabsorption, hypermetabolism and other biochemical changes. The cachexia syndrome causes loss of tissue from three compartments: lean tissue, fat, and bones. It is associated with significantly heightened mortality in addition to the mortality rate caused by the respective cancer or cardiovascular disease, including atherosclerotic cardiovascular disease, heart failure.

The term cachexia syndrome must be distinguished from "wasting" (muscle wasting, cardiac wasting) and from "sarcopenia" though in clinical practice, these conditions are often used overlappingly. "Muscle wasting" denotes loss of skeletal muscle in the absence of weight loss and, similarly, cardiac wasting loss of heart weight in the absence of weight loss. "Sarcopenia", in turn, is defined as muscle wasting due to aging (primary sarcopenia) or illness (secondary sarcopenia).

The cachexia syndrome is initiated and sustained by a severe imbalance which favors catabolic pathways: The major proteolytic pathways of the body—i.e., the ubiquitin-proteasome system, the lysosomal system (cathepsin L and others), the calcium-dependent system (the calpain proteases family), and the caspase-dependent apoptosis system—are chronically stimulated by a multitude of disease-related factors; among them inflammatory cytokines (TNF-α, interleukin-1 and -6, interferon-γ), angiotensin-II, glucocorticoids, melanocortin, as well as reactive oxygen and nitrogen species. The main counter-players—though diminished, outweighed or overridden in the course of disease—are physical activity, the growth hormone-IGF-1-ghrelin axis, insulin, and anabolic steroids.

As to possible therapeutic interventions for the cachexia syndrome and muscle wasting, current pre-clinical and clinical studies have investigated IGF-1, ghrelin and ghrelin analogs, specific androgen receptor modulators (SARMs), myostatin antagonists, cannabinoids (Wang J et al, *New Prospect for Cancer Cachexia: Medical Cannabinoid*, Journal of Cancer 2019, 10(3), 716-720) and antagonists of the melanocortin-4 receptor. Today, the only FDA-approved drugs for cancer-related anorexia/cachexia are progestogens (Garcia V R et al, Cochrane Database of Systematic Reviews 2013, *Megestrol acetate for treatment of anorexia-cachexia syndrome*, https://doi.org/10.1002/14651858-.CD004-310.pub3)

Cancer-associated cachexia affects 50 to 80% of all cancer patients, and gastric as well as pancreatic cancers bear the highest risk of causing the syndrome. Cachexia is the major driver of drastically diminished quality of life in the cancer patients' end-of-life situation, associated with severe dyspnea and edema and contributes largely to the need to be cared for in a hospice setting. Patients in need of hospice care are no longer able to care for themselves in regard of their basic daily activities: daily hygiene (washing and toothbrushing), dressing up, walking small distances in their homes so that the sociopsychological impacts are devastating. The prior art therefore represents a problem, and there is an obvious need for improved therapy and therapeutics.

BRIEF DESCRIPTION OF THE INVENTION

The present application provides a method of treating cardiac cachexia and cardiac wasting in a subject, or suspected of being at risk of cardiac wasting, comprising the administration of an effective amount of relaxin, in particular of human relaxin-2.

Another aspect of the invention relates to the use of human relaxin-2 in a pharmaceutical composition for treating a subject suffering from cardiac cachexia or cardiac wasting, or suspected of being at risk of suffering from cardiac wasting.

A further embodiment relates to a method of treating the symptoms of cardiac decompensation in a subject suffering from advanced cancer, or in a subject suspected of being at risk of suffering from cardiac decompensation as determined and disclosed, comprising the administration of an effective amount of relaxin or human relaxin-2.

A further aspect relates to the use of human relaxin-2 in a pharmaceutical composition for treating the symptoms of cardiac decompensation in a subject suffering from advanced cancer or included in a hospice setting.

Another aspect of the application is a method of treatment or a pharmaceutical composition as disclosed for continuous sc. or iv. infusion of human relaxin-2 in an amount of 5 to 250 micrograms/kg body weight/day.

Some embodiments related to a method of treating cardiac wasting or cardiac cachexia in a subject, or a subject being at risk of cardiac wasting, comprising the administration of an effective amount of human relaxin-2, when the subject is having a sustained ventricular tachycardia of greater than 80 to 100 bpm and/or having an increased resting heart rate of greater than 80 bpm and/or having elevated levels of troponin in blood or serum or plasma which is greater than the 90th percentile of a standard normal distribution and/or a NTproBNP level in blood or serum or plasma which is greater than 1000 pg/ml.

Another aspect relates to the use of human relaxin-2 for preparing a pharmaceutical composition for treating a subject suffering from cardiac wasting or cardiac cachexia, or suspected of being at risk of suffering from cardiac wasting.

A further aspect relates to a therapeutic composition for treating a subject suffering from cardiac wasting or cardiac cachexia, or suspected of being at risk of suffering from cardiac wasting or requiring cardiac decompensation, adapted for an administration of synthetic human relaxin-2 for s.c or i.v. infusion of 10 to 100 µg relaxin-2/kg body weight/day, preferably 25 µg/kg body weight/day.

Some embodiment relate further to a method of treating the symptoms of cardiac decompensation in a subject suffering from advanced cancer, or in a subject suspected of being at risk of suffering from cardiac decompensation, comprising an administration of an effective amount of human relaxin-2.

Some other embodiments relate to a use of human relaxin-2 in a pharmaceutical composition for treating the symptoms of cardiac decompensation in a subject suffering from advanced cancer or included in a hospice setting. These include in particular patients at risk of cardiac wasting who are suffering from severe arrhythmia (sustained ventricular tachycardia), an increased resting heart rate, (>80 bpm), and/or elevated cardiac markers like troponin (>90th percentile of a standard distribution) or NTproBNP (>1000 pg/ml blood/serum/plasma).

pb3 kinase.

DETAILED DESCRIPTION OF THE INVENTION

Recent pre-clinical and clinical research indicates an overlap between heart failure and end-stage cancer syndrome. Terminally-ill cancer patients often show signs of cardiac dysfunction such as severe arrhythmia, increased resting heart rate, as well as elevated cardiac markers such as troponin or NTproBNP while not having a cardiovascular history. The cardiac dysfunctions can not be assigned to a cardiotoxic cancer chemotherapy and possess independent prognostic relevance for survival. End-stage heart failure may cause cachexia syndrome like end-stage cancer disease. The cancer-associated cachexia syndrome (hereinafter cancer cachexia) and the heart failure associated cachexia syndrome (hereinafter cardiac cachexia) likely share a common cachectic pathophysiology. This has not yet had a substantive impact on clinical strategies to improve quality of life in terminal cancer while there are some elder studies which evaluate muscle wasting and cardiac dysfunction and wasting in individuals. In both cases, cachexia is a severe complication that adversely affects the underlying disease and is associated with high rates of mortality.

The mortality of patients rises once cardiac cachexia has developed to 50% over 18 months. The prevalence of this syndrome is approximately 15% in cardiac heart failure, but wasting is present in more than 60% of the patients (Anker S D et al. in *Wasting as independent risk factor for mortality in chronic heart failure*, Lancet 1997, 349(9058):1050-3). Increased levels of norepinephrine, angiotensin II, pro-inflammatory cytokines, and glucocorticoids in combination with reduced levels of ghrelin and IGF-1 are established factors to induce a catabolic state. This may be partially reversed by an administration of relaxin-2 (Dschietzig T B, *Myostatin—From the Mighty Mouse to cardiovascular disease and cachexia*. Clin Chim Acta 2014, 433:216-224). The up-regulated myostatin in myoblasts creates a link to the clinical situation in chronic heart failure and this is circumstantial evidence in terms of myostatin's role in cardiac cachexia, in particular as heart-specific myostatin deletion is known to prevent weight decrease in the leg muscles. Consequently, an administration of relaxin-2 may have a beneficial effect and a reverse of muscle loss. Judging from murine models of cancer cachexia, the syndrome is a consequence of circulating factors secreted both from healthy tissue and tumor cells. Myostatin inhibition, in turn, largely abrogates this state.

Further beneficial effects of relaxin in cardiac wasting my be derived thereof that relaxin can mitigate neurohumoral activation by a release of the compensatory mediator atrial natriuretic peptide (ANP) and by promotion of the clearance of endothelin-1 (ET-1). Relaxin-1 further improve a compromised haemodynamics by increasing atrial myocardial inotropy, inducing peripheral vasodilation and expediting ventricular filling. Reversal of myocardial fibrosis alleviates cardiac remodeling and better renal perfusion expedites salt and water diuresis. The numerous anabolic effects of relaxin-2 are best summarized by data obtained from the first placebo-controlled clinical trials (Seibold J R et al, *Recombinant human relaxin in the treatment of scleroderma. A randomized, double-blind, placebo-controlled trial*. Ann Intern Med 2000, 132:871-879). The continuous subcutaneous infusion of relaxin over 24 weeks caused sustained physiological changes which closely mimicked those seen in human pregnancy. An increased blood volume, lower plasma osmolality, increased cardiac output owing to decreased cardiac afterload, decreased systolic and diastolic blood pressure, increased renal and endometrial blood flow, and increased glomerular filtration rate are clearly factors counter-acting cachexia and cardiac wasting. Consequently, the inventors can describe relaxin as a pleiotropic hormone and antagonist to weight loss, cachexia and cardiac wasting similar to insulin (Dschietzig T B et al in *Relaxin—A pleiotropic hormone and its emerging role for experimental and clinical therapeutics*. Pharmacol Ther 2006, 112(1):38-56). In essence, without wishing to be bound by hypothesis, it seems that relaxin-2 counteracts phosphatidylinositol 3-kinase and a number of unrelated proteins at higher concentrations without incurring the toxic effects of any of the conventional pi3 kinase inhibitors. As of January 2019, three PI3K inhibitors have been approved by the FDA for clinical use in humans: the PIK3CD inhibitor idelalisib (July 2014, NDA 206545), the dual PIK3CA and PIK3CD inhibitor copanlisib (September 2017, NDA 209936), and the dual PIK3CD and PIK3CG inhibitor duvelisib (September 2018, NDA 211155). The inhibition of the pathway is considered a promising anti-cancer therapeutic strategy. The toxic effects of relaxin-2 are much lower and therefore an administration of relaxin-2 may a potent drug for for an inhibition of the phosphatidylinositol 3-kinase /AKT/GSK-3 beta pathway (Yang W et al, in *Myostatin induces cyclin D1 degradation to cause cell cycle arrest through a phosphatidylinositol 3-kinase /AKT/GSK-3 beta pathway and is antagonized by insulin-like growth factor 1*. J Biol Chem 2007, 282:3799-808).

Differentiation Between Cardiac Wasting and Cardiac Cachexia

In a retrospective study, individuals who had died of cancer and cancer-free controls who died of other, non-cardiovascular reasons were analysed for cardiac muscle wasting (Barkhudaryan A et al, in Cardiac muscle wasting in individuals with cancer cachexia, ESC Heart Fail 2017, 4(4):458-467). Cancer cachexia was defined therein by a body mass index (BMI) of less than 20.0 and a oedema-free body weight loss of greater 5.0% during the previous year. The pathology reports were analysed for BMI, heart weight (HVV), and left and right ventricular wall thicknesses (LVWT and RVWT, respectively). Cancer cachexia was detected in about 30 percent of the cases. The individuals with cancer cachexia had a significantly lower heart weight than non-cachectic subjects and the BMI basically correlated with a diminished heart weight in cases of gastrointestinal cancer, lung cancer, and pancreatic cancer. Cancer cachexia clearly caused a catabolic/anabolic imbalance which affected all body components, including skeletal musculature and the heart muscle (loss of heart muscle weight).

The cachexia syndrome comprises multiple pathophysiologic pathways which lead to extreme fatigue and weakness. The metabolic, neurohormonal, and immune abnormalities cause an altered regulation of proliferation, differentiation, apoptosis, and metabolism in the skeletal muscle, finally resulting in a symptomatic exercise intolerance. There are no viable treatment strategies against cardiac cachexia or cardiac wasting.

Diagnosis of Cardiac Wasting

A diagnosis of cardiac wasting may be made, e.g. for cancer patients, in case of a sustained ventricular tachycardia which is characterized by a ventricular rhythm faster than 80 to 100 bpm lasting at least 30 seconds. Ventricular tachycardia may be defined as a wide complex tachycardia originating from one of the ventricles, and which is not due to aberrant conduction such as a bundle branch block. A diagnosis of cardiac wasting would typically require the absence of a structural heart disease (e.g. myocardial infarction, active ischemia, cardiomyopathy, valvular disease, arrhythmogenic right ventricular cardiomyopathy, left ventricular noncompaction, or other disorders of the myocardium), channelopathy, drug toxicity by the respective cancer therapy, or electrolyte imbalance. Sustained ventricular tachycardia typically results in hypotension and symptoms of weakness, syncope, and palpitations. An increased resting heart rate (>80 bpm) and elevated cardiac markers of troponin (greater the 90th percentile of a standard normal distribution) or NTproBNP (>1000 pg/ml blood/plasma/serum) support a diagnosis of cardiac wasting in case of unclear symptoms of a cachexia syndrome (loss of body mass, BMI).

Treating a Subject

In some cases, the method comprises the administration of an effective amount of relaxin or human relaxin-2, or a use of human relaxin-2 in a pharmaceutical composition for treating a subject suffering from cardiac wasting or suspected of being at risk of suffering from cardiac wasting as determined and disclosed.

Also disclosed herein in some embodiments are methods that can comprise treating a disease in a subject as disclosed herein. In some cases, treating a disease can comprise regulating the beating of a heart of a subject. In some cases, treating a disease can comprise administering a medicament to a subject as described herein. In some cases, treating a disease can result in a reduction of plasma levels of natriuretic peptides. In some cases, natriuretic peptides can comprise ANP and/or BNP.

In some cases, treating a disease can comprise an anti-cachexic effect. In some cases, an anti-cachexic effect can comprise a clinical benefit. In some cases, treating a disease can result in a reduction in a risk of sudden cardiac death. In some cases, treating a disease can result in a reduction of weight loss.

In some cases, treating a disease can result in an improvement of symptom status. In some cases, a symptom can comprise shortness of breath, fatigue status, muscle strength, exercise capacity, and any combination thereof. In some cases, a treatment can aim to improve patients' quality of life, symptoms, general wellbeing, cardiac health, survival, duration of hospitalization, cost of hospitalization, or any combination thereof.

EXAMPLES

While preferred embodiments have been shown and described herein, it will be obvious to those skilled in the art that such embodiments are provided by way of example only. Numerous variations, changes, and substitutions will now occur to those skilled in the art without departing from the disclosure provided herein. It should be understood that various alternatives to the exemplary embodiments described herein may be employed.

Example 1—Human Relaxin-2 for Treating Cardiac Decompensation and Cardiac Wasting in Patients with Advanced Cancer 30 patients with advanced cancer in the hospice setting are included randomized and double-blind in a clinical study to a 10-day continuous sc. or iv. infusion of either synthetic human relaxin-2 (25 micrograms/kg body weight/day) (n=20) or placebo (n=10). The following exploratory clinical end-points are assessed at baseline and during treatment (day 3 and day 10):

1. Patients are asked to report their current level of both dyspnea and general wellbeing relative to baseline using seven-level Likert scales.

2. In the context of this study, ability of self-care is defined as ability to perform the measures of personal daily hygiene (washing, tooth-brushing) without help.

3. Congestion is assessed as percentage of patients showing ankle edema or rales upon auscultation.

4. Plasma levels of NT-proBNP (N-terminal fragment of pro-brain natriuretic peptide), a biomarker of cardiac decompensation, are determined.

5. The four-meter gait speed (4MGS) is measured.

The following clinical results are obtained:

TABLE 1

Level of Dyspnea

| | Day 3 | | Day 10 | |
| --- | --- | --- | --- | --- |
| | Markedly or moderately improved | Markedly or moderately worsened | Markedly or moderately improved | Markedly or moderately worsened |
| Placebo | 1 (10) | 3 (33) | 1 (10) | 6 (60) |
| Relaxin | 8 (40)[#] | 1 (5)[#] | 12 (60)[#] | 1 (5)[#] |

Table 1: Level of dyspnea relative to baseline on a seven-level Likert scale. Values are absolute numbers with percentages in parentheses. [#]$P < 0.05$ as determined by Chi-square test.

TABLE 2

Ability of Self-Care

|  | Baseline | Day 3 | Day 10 |
|---|---|---|---|
| Placebo | 3 (33) | 4 (40) | 2 (20) |
| Relaxin | 5 (25) | 7 (35) | 17 (85)* |

Table 2: Ability of Self-Care on yes-or-no level. Values are absolute numbers with percentages in parentheses. #, P < 0.05 as determined by Chi-square test.

TABLE 3

Level of General Wellbeing

|  | Day 3 | | Day 10 | |
|---|---|---|---|---|
|  | Markedly or moderately improved | Markedly or moderately worsened | Markedly or moderately improved | Markedly or moderately worsened |
| Placebo | 2 (20) | 4 (40) | 1 (10) | 5 (50) |
| Relaxin | 9 (45)# | 2 (10)# | 11 (55)# | 1 (5)# |

Table 3: Level of general wellbeing relative to baseline on a seven-level Likert scale. Values are absolute numbers with percentages in parentheses. #P < 0.05 as determined by Chi-square test.

TABLE 4

Congestion

|  | Baseline | | Day 3 | | Day 10 | |
|---|---|---|---|---|---|---|
|  | Moderate or severe edema | Moderate or severe rales | Moderate or severe edema | Moderate or severe rales | Moderate or severe edema | Moderate or severe rales |
| Placebo | 8 (80) | 7 (70) | 8 (80) | 8 (80) | 7 (70) | 6 (60) |
| Relaxin | 15 (75) | 16 (80) | 10 (50) | 8 (40)# | 6 (30)# | 5 (25)# |

Table 4: Edema and rales are clinically assessed and rated on a four-level scale (none, mild, moderate, severe). Values are absolute numbers with percentages in parentheses. #P < 0.05 as determined by Chi-square test.

TABLE 5

Plasma NT-proBNP

|  | Baseline | Day 3 | Day 10 |
|---|---|---|---|
| Placebo | 3124 (480-3598) | 2895 (405-3381) | 3424 (580-3982) |
| Relaxin | 3438 (597-4175) | 1813 (294-2558)* | 778 (172-1352)* |

Table 5: Median (IQR) of NT-proBNP given in pg/ml. IQR, inter-quartile range. *P < 0.05 as determined by a non-parametric two-way ANOVA followed by Mann-Whitney U-test.

TABLE 6

Four-Meter Gait Speed

|  | Baseline | | Day 3 | | Day 10 | |
|---|---|---|---|---|---|---|
|  | Speed (m/s) | Unable to walk 4 m | Speed (m/s) | Unable to walk 4 m | Speed (m/s) | Unable to walk 4 m |
| Placebo | 0.52 (0.12-0.82) | 3 (30) | 0.60 (0.20-0.89) | 2 (20) | 0.48 (0.08-0.72) | 4 (40) |
| Relaxin | 0.56 (0.10-0.75) | 7 (35) | 0.66 (0.20-0.85) | 5 (25) | 0.86* (0.39-1.15) | 3 (15)# |

Table 6: Four-meter gait speed in m/s: median (IQR). IQR, inter-quartile range. Also given: absolute number (%) of patients unable to walk 4 meters. *P < 0.05 as determined by a non-parametric two-way ANOVA followed by Mann-Whitney U-test. #P < 0.05 as determined by Chi-square test.

CONCLUSION

The study demonstrates that continuous treatment with synthetic human relaxin-2 for 10 days markedly improves the clinical status of hospice patients with advanced, incurable cancer. Relaxin-2 ameliorates clinical signs of cardiac decompensation such as congestion, dyspnea, and circulating NT-proBNP as well as in respect of cardiac wasting and cardiac cachexia which, in turn, enables patients to perform better in basic daily activities (self-care, mobility) and which enables general wellbeing.

The invention claimed is:

1. A method of treating a patient diagnosed with cardiac wasting or cardiac cachexia or being at risk of cardiac wasting, comprising the administration of an effective amount of human relaxin-2, wherein said method comprises administering human relaxin-2 at 10 to 100 μg relaxin-2/kg body weight/day.

2. The method of claim 1, wherein the patient is diagnosed when having a sustained ventricular tachycardia of greater than 80 to 100 bpm and/or having an increased resting heart rate of greater than 80 bpm and/or having elevated levels of troponin in blood or serum or plasma, which is greater than the 90th percentile of a standard normal distribution and/or an N-terminal prohormone B-type natriuretic peptide (NT-proBNP) level in blood or serum or plasma which is greater than 1000 pg/ml.

3. The method of claim 1, which comprises administering human relaxin-2 at 25 μg/kg body weight/day.

4. The method of claim 1, which comprises subcutaneous or intravenous infusion of human relaxin-2 at a rate of 10 to 100 μg/kg body weight/day.

5. The method of claim 1, which comprises subcutaneous or intravenous infusion of human relaxin-2 at a rate of 25 μg/kg body weight/day.

6. The method of claim 1, which comprises administering said human relaxin-2 with a patch pump prefilled with a pharmaceutical composition comprising human relaxin-2.

* * * * *